United States Patent
Armbruster et al.

(10) Patent No.: US 8,834,935 B2
(45) Date of Patent: Sep. 16, 2014

(54) BONE GRAFT AND BIOCOMPOSITE FOR PROSTHETIC DENTISTRY

(75) Inventors: Franz Paul Armbruster, Bobenheim-Roxheim (DE); Rolf Briant, Cologne (DE)

(73) Assignee: Armbruster Biotechnology GmbH, Bensheim (DE)

( * ) Notice: Subject to any disclaimer, the term of this patent is extended or adjusted under 35 U.S.C. 154(b) by 0 days.

(21) Appl. No.: 13/381,700

(22) PCT Filed: Jul. 5, 2010

(86) PCT No.: PCT/EP2010/059588
§ 371 (c)(1),
(2), (4) Date: Jan. 3, 2012

(87) PCT Pub. No.: WO2011/000970
PCT Pub. Date: Jan. 6, 2011

(65) Prior Publication Data
US 2012/0107407 A1    May 3, 2012

(30) Foreign Application Priority Data

Jul. 3, 2009   (EP) .................................. 09164607
Apr. 11, 2010  (EP) .................................. 10159575

(51) Int. Cl.
*A61L 27/42*   (2006.01)
*A61L 27/36*   (2006.01)

(52) U.S. Cl.
USPC ......................................................... 424/491

(58) Field of Classification Search
CPC .. A61K 2039/505; A61K 38/00; A61K 48/00; A61L 2430/02; A61L 27/46; C07K 14/47
USPC ....................................................... 424/491
See application file for complete search history.

(56) References Cited

U.S. PATENT DOCUMENTS

| | | | |
|---|---|---|---|
| 6,340,477 B1 * | 1/2002 | Anderson | 424/488 |
| 6,811,776 B2 * | 11/2004 | Kale et al. | 424/93.7 |
| 7,022,522 B2 * | 4/2006 | Guan et al. | 435/395 |
| 7,270,813 B2 * | 9/2007 | Shimp et al. | 424/93.7 |
| 2003/0082808 A1 | 5/2003 | Guan et al. | |
| 2004/0052860 A1 * | 3/2004 | Reid et al. | 424/535 |
| 2004/0096509 A1 * | 5/2004 | Hutchens et al. | 424/488 |

FOREIGN PATENT DOCUMENTS

| | | | | |
|---|---|---|---|---|
| DE | WO2005/104988 A2 * | 11/2005 | | 424/491 |
| EP | 1 084 719 A1 | 3/2001 | | |
| WO | WO 2005/104988 A2 | 11/2005 | | |

OTHER PUBLICATIONS

Reichardt, D. et al. "Injectable and PLGA coated beta-TCP granules hardening in situ: an in vitro study", European Cells and Materials, vol. 11, Suppl 2, 2006, p. 27.*

Reichardt, D. et al. "Injectable and PLGA coated beta-TCP granules hardening in situ: an in vitro study", European Cell and materials, vol. 11, Suppl. 2, 2006, p. 27.*

D. Reichardt et al., "Injectable and PLGA coated beta-TCP granules hardening in situ: an in vitro study", *European Cells and Materials*, vol. 11(2), 2006, p. 27.

* cited by examiner

*Primary Examiner* — Janet Epps-Smith
*Assistant Examiner* — Audrea Buckley
(74) *Attorney, Agent, or Firm* — Dickstein Shapiro LLP

(57) ABSTRACT

A bone graft or biocomposite for treating osseous defects and neogenesis of bone which is a composite of a biodegradable polymer and granules of beta-tricalciumphosphate, further comprising as active ingredient and embedded in the biodegradable polymer a physiologically effective amount of underglycosylated recombinant human BSP as a multi-dental clathrate with a basic organic compound which simulataneously is active as a plasticizer for the biodegradable polymer. The biocomposite is moldable and shapeable, hardens rapidly in situ when placed by surgery or prosthetic dentistry and which furthers osseous repair and the healing of damage or diseased tissues and lesions.

17 Claims, 13 Drawing Sheets

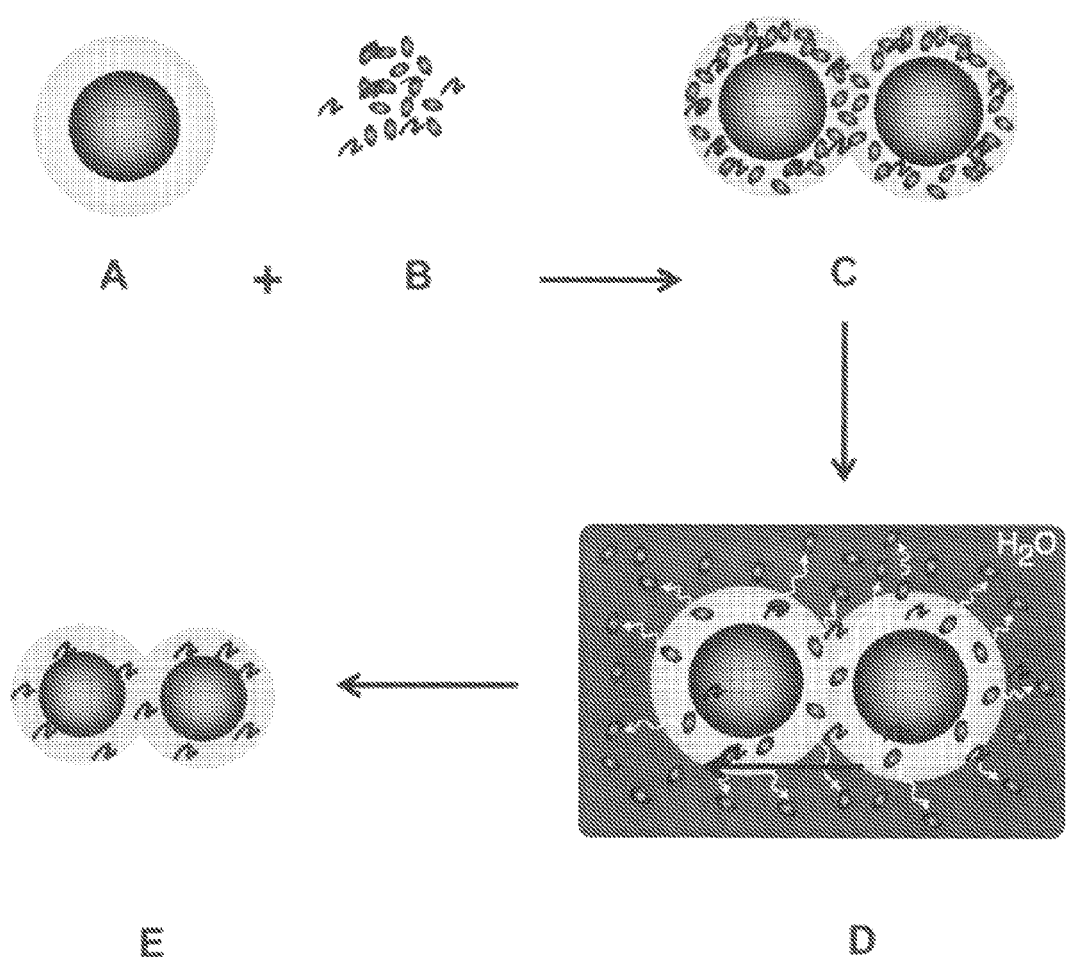

Fig 5 (continued)
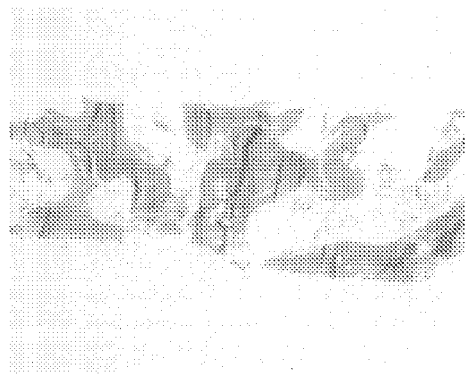
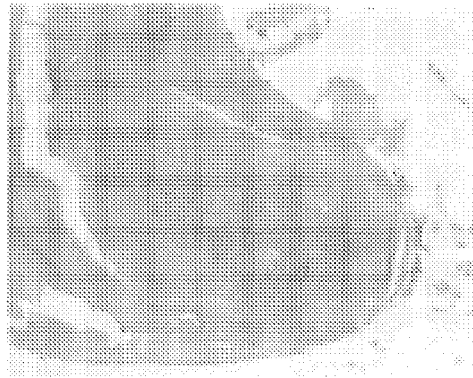

Fig 5 (continued)
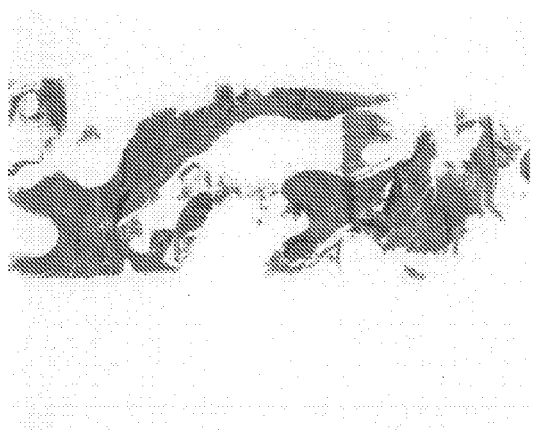
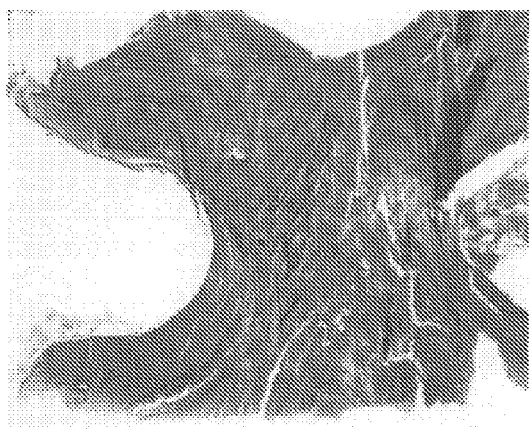

Fig 6
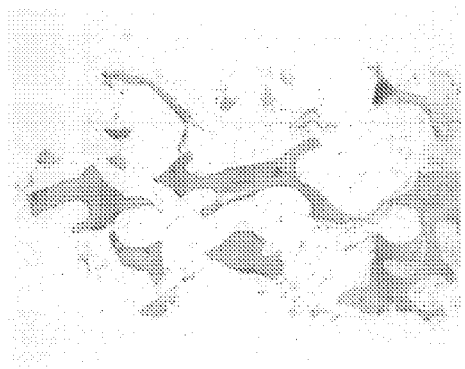
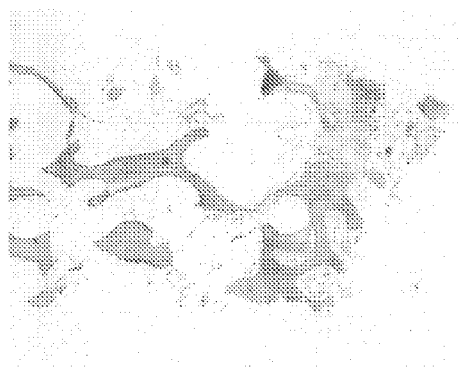
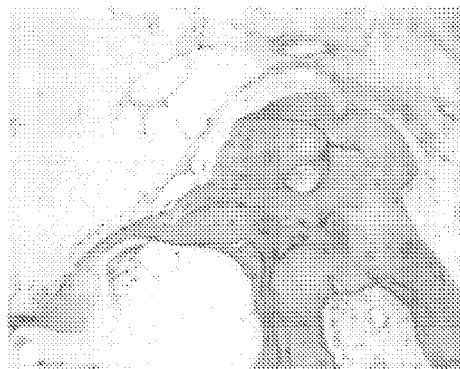
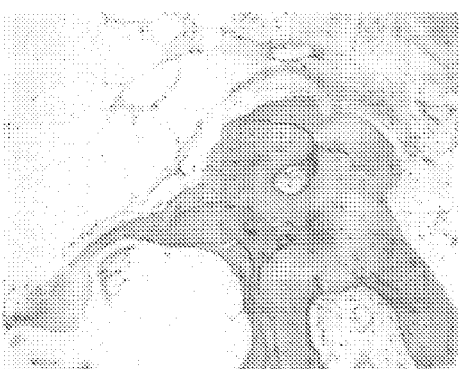

Fig 6 (continued)
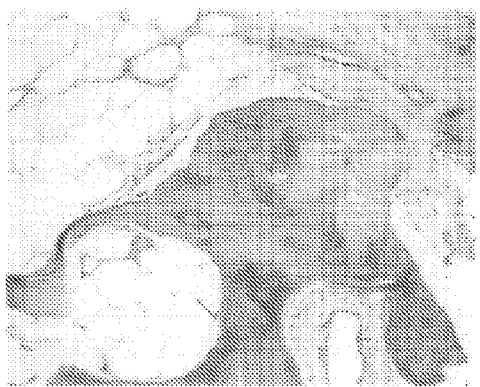
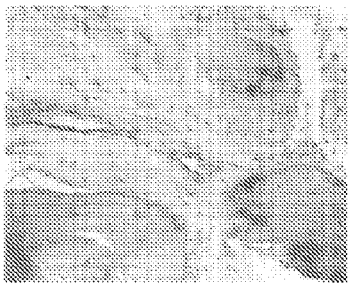
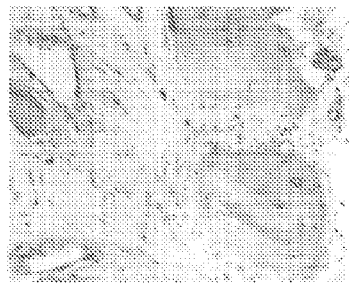

Fig. 7
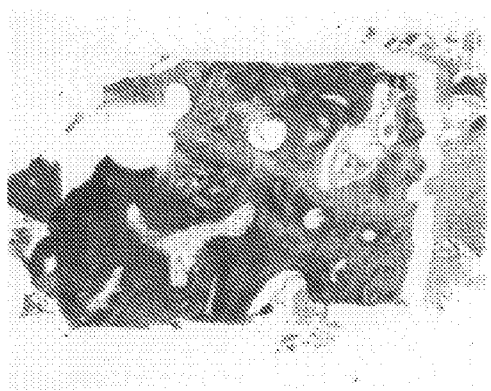
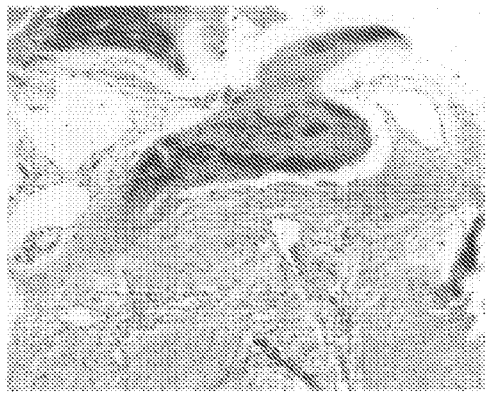
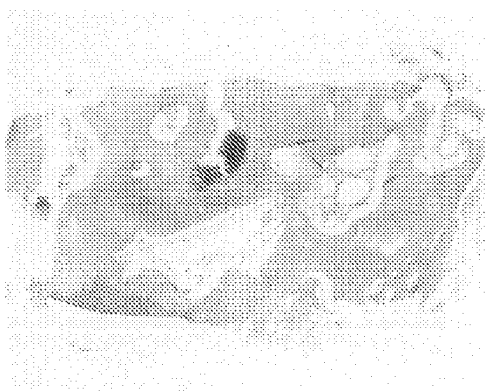

Fig. 7 (continued)
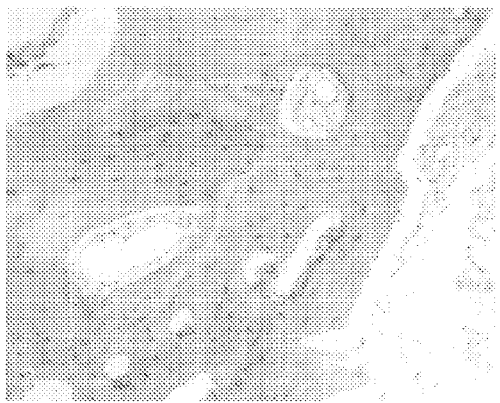
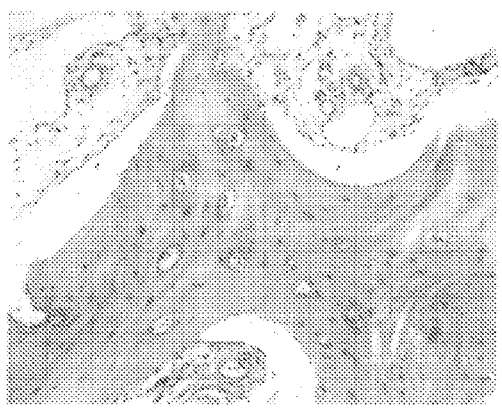

BONE GRAFT AND BIOCOMPOSITE FOR PROSTHETIC DENTISTRY

FIELD OF THE INVENTION

The invention relates to bone grafts and biocomposites made of a base material comprising granules of tricalcium phosphate and a resorbable polymer or co-polymer. The invention relates in particular to methods and compositions for accelerating and improving the healing of bone and soft tissue lesions in the course of prosthetic dentistry.

BACKGROUND OF THE INVENTION

The stability of bone implants depends greatly on their ingrowth properties. For dental implants to work, there must be sufficient bone in the jaw, and the bone has to be strong enough to hold and support the implant. Where there is insufficient or inadequate maxillary or mandibular bone in terms of depth or thickness, grafts are used in prosthetic dentistry to provide secure integration with the dental implant. Conventional grafts include the patient's own bone (autografts), processed bone from cadaver (allografts); bovine bone or coral (xenografts); and synthetic bone-like or bone-mimetic materials.

In a typical procedure, the dentist or oral surgeon creates a large flap of the gingiva or gum to expose the jawbone at the graft site, installs some types of block and onlay grafts in and on existing bone and finally takes measures to repel unwanted infections. The gingiva is then sutured over the site and the graft site allowed to heal for several weeks or months. The healing involves a complicate cascade of adaptive cellular responses such as differentiation, migration, attachment, proliferation, extracellular matrix synthesis and finally mineralization. The osteointegration of the graft or implant into the surrounding bone is however poorly understood. Osteoinduction and osteogenesis involve a plethora of growth factors and there are numerous further molecules which are said to contribute to these processes.

The bone morphogenic proteins (BMP) are the only growth factors known to induce bone formation heterotopically. Supplementary doses of BMPs boost the bone healing by inducing undifferentiated mesenchymal cells to differentiate into osteoblasts. Bone grafts and implants however shall result in a live vascular bone which is very much like natural. U.S. Pat. No. 5,478,237 (Ishikawa) discloses an implant coated with a layer of hydroxyapatite, WO 02/078759 (Stratec Medical AG) an implant having a layer of a porous metal oxide comprising amorphous and nanocrystalline calcium phosphate and hydroxyapatite, WO 02/085250 (KERAMED GmbH) an implant wherein a coating of resorbable calcium phosphate phases contains adhesion and signal proteins such as bone sialoprotein (BSP), bone morphogenic protein (BMP), fibronectin, osteopontin (OPN), ICAM-1, VCAM and derivatives thereof. Further grafts and implants of this type are described in EP 1 166 804 A2 (Merck, Darmstadt) and WO 99/08730 (Children's Medical Center Corporation). DE 100 37 850 A1 (Jenissen H) and WO 03/059407 A1 (Straumann Holding AG) describe grafts and implants treated with ubiquitin or transforming growth factor (TGF) or systemic hormones such as osteostatin, osteogenie and osteogrowth peptide (OGP). U.S. Pat. No. 7,229,545 B2 (Biomet Deutschland GmbH) teaches bone-analogous coatings made of a collagen matrix mineralised with calcium phosphate, EP 1 442 755 A1 (Depuy Products) a bioactive ceramic coating comprising osteogenic proteins OP-1, BMP-7 and non-collagenous bone matrix proteins. Osteogenic activities have further been reported for fibroblast growth factor (FGF), transforming growth factor-$\beta$ (TGF-$\beta$), platelet-derived growth factor (PDGF), insulin growth factor (IGF) and family members of the foregoing.

WO 2005/104988 (Armbruster et al) claims implants and bone repair matrices treated with an underglycosylated human rBSP. The implants are made of titanium, zirconium, ceramic, metal alloys or stainless steel and may be coated with amorphous or crystalline hydroxyapatite and/or calciumphosphate. Such bone-mimetic coatings however suffer from the disadvantage that they tend to loosen from the substrate with time which affects the long-term stability of implants.

WO 03/047646 (Inion Ltd., Tampere, Finland) teaches bone grafts that can be fashioned into medical implants. The graft or implant is made of a base material comprising a matrix of resorbable polymers or copolymers, and N-methyl-2-pyrrolidone (NMP). Reichhardt et al describe in European Cells and Materials 2006, 11(2):27f a bio-composite comprising granules of beta-tricalcium phosphate (beta-TCP) coated with a copolymer of polyglycolic and polylactic acid. The biocomposite can be made moldable for placement by mixing it with N-methyl-pyrrolidone. Nair et al disclose in J. Biomater. Appl. 2006, 20:307-24 dental grafts and implants wherein the beta-TCP granules are held together by thermal fusion of a polyglycolic-polylactic acid copolymer. The beta-TCP particles are described as inhibiting the differentiation and proliferation of mesenchymal stem cells to osteoblasts and osseous healing. Wang et al. describe in J. Orth. Res., 2002, 20:1175ff such a kind of inhibition too for metal abrasion particles as well as for worked and large surface areas.

U.S. Pat. No. 6,458,763 (Peterson et al.) claims a bioactive composition for the repair of damaged or diseased bone and cartilage. The bioactive composition is administered via a delivery vehicle comprising a pharmaceutically acceptable basis and physiological mineral fillers such as tricalcium phosphate, hydroxyapatite, gypsum and the like. When a hole is drilled into the rat calvaria at or adjacent the parietal eminence and the bioactive composition pumped to the site of the calvarial defect over a period of 14 days using an osmotic pump, then there is observed an in vivo induction of bone tissue growth around the drilled hole. The method of administration and the composition are clearly not suitable for prosthetic dentistry.

WO 94/13310 (Höök et al) claims a composition comprising as active ingredient a competitor peptide which seems to fight the attachment of *Staphylococcus aureus* to bone tissue as well as osteomyelitis (Ryden et al., 1989, Eur. J. Biochem. 184: 331f).

The prior art notwithstanding represents a problem as dental implants often give rise to a periodontal condition called peri-implantitis caused by an infection introduced during surgery or a failure by the patient to follow correct oral hygiene routines. While implantitis can be dealt with by a course of antibiotics and special oral rinses in the days prior and past surgery, a pre-emptive treatment of peri-implantitis as well as improved wound and soft tissue healing would be more desirable. Aseptic loosening, inflammation reactions and long-term stability of endosseous implants further continue to remain a problem. Despite bioactive coatings there is still a considerable period of time between surgery and osteointegration until when bone grafts and endosseous tooth implants can withstand typical pressure, shear and tensile forces.

It is in particular an object of the instant invention to provide a graft material which allows easy placement as well as methods and compositions for furthering the healing of bone and soft tissue lesions in the course of prosthetic dentistry.

SUMMARY OF THE INVENTION

This object has been achieved by a biocomposite as claimed in claim 1. Further embodiments of the invention are disclosed in the dependent claims.

The bone graft of the invention for treating osseous defects and neogenesis of bone is a composite of a biodegradable polymer and granules of beta-tricalciumphosphate and obtained by the steps of:

providing an osteoinductive mixture, which is a dispersion or solution on the basis of an organic compound having at least one nitrogen-containing basic group and of a physiologically effective amount of underglycosylated recombinant human BSP obtained under non-denaturing conditions, where the underglycosylated recombinant human BSP is present in said osteoinductive mixture as a salt or complex which has reduced affinity for calcium, hydroxyapatite and complement factor H than regular human BSP present in human serum, and, optionally, a pharmaceutically acceptable excipient or carrier;

providing an osteoconductive mixture on the basis of granules of tricalcium diphosphate ($Ca_3(PO_4)_2$ in beta crystal form, which granules are coated with a biodegradable polymer or co-polymer and, optionally, a pharmaceutically acceptable excipient or carrier, which osteoconductive mixture is moldable and shapeable and rapidly hardening in situ when placed by surgery or prosthetic dentistry, and combining said osteoinductive and osteoconductive mixture shortly before or during placement to obtain a bone graft material which furthers osseous repair and the healing of damage or diseased tissues and lesions.

In a second aspect of the invention the osteoinductive human BSP is underglycosylated human BSP expressed and obtained from eukaryotic cells grown under serum-free conditions.

In a third aspect of the invention, the underglycosylated human BSP has been obtained from colostrum or mother milk.

The organic compound used in the present invention is preferably one having at least one ring nitrogen-containing basic group. Said organic compound may be preferably both a dispersing agent and a plasticizer of the biodegradable polymer or co-polymer and may be selected from the group consisting of N-isopropylpyrrolidone, N-methylpyrimidine, N-ethylpyrimidine, N-methylpyrrolidone (1-methyl-2-pyrrolidone), N-ethylpyrrolidone, N-propylpyrrolidone, N,N-diethyl-1,4-butanediamine, 1-(2-aminoethyl)-piperazine, 2-(1-pyrrolidyl)ethylamine, 4-amino-2-methoxy-pyrimidine, 2-dimethylamino-ethanol, 1-(2-hydroxyethyl)-piperazine, 4-(2-hydroxyethyl)-morpholine, 2-mercapto-pyrimidine, 2-mercaptobenzimidazole, N,N-dimethyl-1,3-propanediamine, 4-(2-amino-ethyl)-pyridine, 2-amino-6-methoxybenzothiazole, 4-(aminoethyl)pyridine, N,N-diallyl-melamine, 3-amino-1,2,4-triazole, 1-(3-aminopropyl)-imidazole, 4-(2-hydroxyethyl)-pyridine, 1-(2-hydroxyethyl)-imidazole, 3-mercapto-1,2,4-triazole.

In a further aspect of the invention, said biodegradable polymers or copolymers are selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycaprolactone, poly(L-lactide-co-caprolactone), poly(D,L-lactide-co-caprolactone) polytrimethylenecarbonates, poly(L-lactide-co-trimethylenecarbonate), poly(D,L-lactide-co-trimethylenecarbonate), polydioxanones, polylactic acid polymers, polyglycolic acid polymers, copolymers of polylactic acid and polyglycolic acid, poly-hydroxybutyrates, polyhydroxyvalerates polydioxanones, polyorthoesters, polycarbo-nates, polytyrosinecarbonates, polyorthocarbonates polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof.

Another aspect of the invention relates to the osteoconductive component for use in prosthetic dentistry which may preferably comprise coated granules of tricalcium phosphate ($Ca_3(PO_4)_2$ having diameters of 300 to 800 µm, preferably 400 to 700 µm. The biocomposite of the invention may preferably comprise more than 50 volume percent of granules of beta tricalcium phosphate, between 10 to 40 volume percent of a polymer base including one or more biodegradable polymers and copolymers, 0.5 to 10 volume percent of a first osteoinductive mixture which increases plasticity and workability of the biocomposite and as solvent or dispersion agent of BSP. Said composite may comprises human rBSP in an amount from 1 to 200 µg/mL (w/v) composite. Preferably, said osteoinductive mixture may comprise human rBSP in an amount from 1 to 200 µg/mL (w/v) before hardening.

In accordance with the invention, said biodegradable polymer may be a copolymer of polylactic acid and polyglycolic whose composition is 50 to 80 percent lactic acid and 20 to 50 percent glycolic acid. Said PLA:PGA co-polymer may have a selected weight average molecular weight range between about 25,000 and about 1,000,000. The bone graft material should preferably have a Young's Modulus between 1 GPa and about 100 Gpa after hardening.

A further aspect of the invention relates to a method of preparing a bone graft having osteoinductive and osteoconductive properties comprising the steps of:

providing an osteoinductive mixture, which is a dispersion or solution on the basis of an organic compound having at least one nitrogen-containing basic group and of a physiologically effective amount of underglycosylated recombinant human BSP;

providing an osteoconductive mixture on the basis of granules of tricalcium diphosphate ($Ca_3(PO_4)_2$ in beta crystal form, which granules are coated with a biodegradable polymer or co-polymer; and combining said osteoinductive and osteoconductive mixtures to obtain a composite material which is initially moldable and shapeable and hardens in situ when placed by surgery or prosthetic dentistry.

A method of providing a bone graft material with properties which further the healing of wound and soft tissue lesions, comprising the step of combining the bone graft material with a dispersion or solution on the basis of an organic compound having at least one nitrogen-containing basic group and a physiologically effective amount of underglycosylated recombinant human BSP.

The invention further comprises a method of furthering the healing of wound and soft tissue lesions which comprises the administration or use of a biocomposite as defined above. The application or use may comprise a forming of said biocomposite into an implant device selected from the group consisting of: tissue scaffolds, granular bone graft substitute material, two-phase osteochondral implants, weight-bearing bone implants, no- and low-weight-bearing implants or fixation devices, tacks, pins, screws, bone on lays, and films.

The invention further extends to resorbable polymer composition having wound healing properties comprising a polymer matrix of resorbable polymer(s) or copolymer(s), N-methyl-2-pyrrolidone (NMP) and a pharmaceutically effective amount of human rBSP, preferably designed as suture material. The invention also extends to method of treatment wherein a solution of NMP and human rBSP is added or applied to the implant or wound, re- or postoperatively.

The principles of the present invention are particularly useful for an implant, which is composed of a base body, a spacer assembly composed of a spacer bushing bottom or base element and a spacer bushing top or ring member. The base body is provided with an internal bore that has internal threads. The base body adjacent an upper edge or end, has a recess, which is of a larger diameter than the bore to provide a stop shoulder. To provide means for preventing axial twisting, the stop shoulder is provided with uniformly, circumferentially spaced recess interlocking pockets so that a ceramic tooth can be screwed on.

BRIEF DESCRIPTION OF THE DRAWINGS

The present invention, its feature and advantages will now be described by way of example only with reference to the accompanying drawings, wherein:

FIG. 1 is schematic representation of the steps for preparing the biocomposite of the invention;

FIGS. 6/01-13 microscopic views of a bone specimen (D78—length 0.5 cm) from a another rhBSP/TCP-biocomposite implant, also taken 12 weeks after placement—preparation, fixation and staining with Masson-Goldner's trichrome stain or toluidine blue or haematoxylin paired with eosin;

FIGS. 7/01-09—microscopic views of a third histologic specimen (D59—length 0.6 cm) taken from a rhBSP/TCP biocomposite 3 months after surgery—preparation, fixation and staining with Masson's trichrome stain, toluidine blue or haematoxilin paired with eosin.

DETAILED DESCRIPTION OF THE INVENTION AND PREFERRED EMBODIMENTS

Figure 2A:
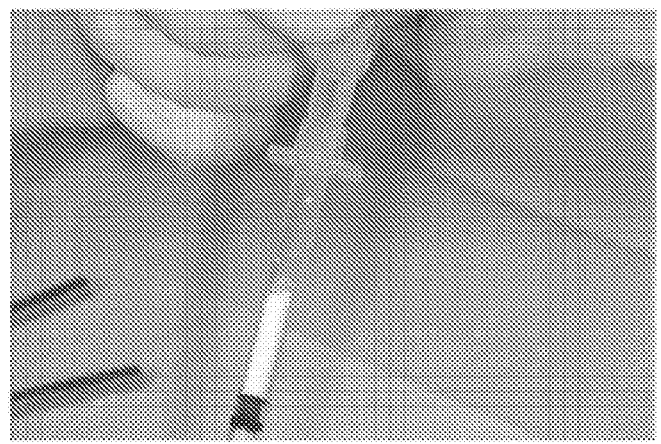
FIGS. 2A-C are photographs of showing the preparation of a biocomposite comprising human rBSP/NMP and bioresorbable polymer-coated β-TCP granules.
Figure 2B:
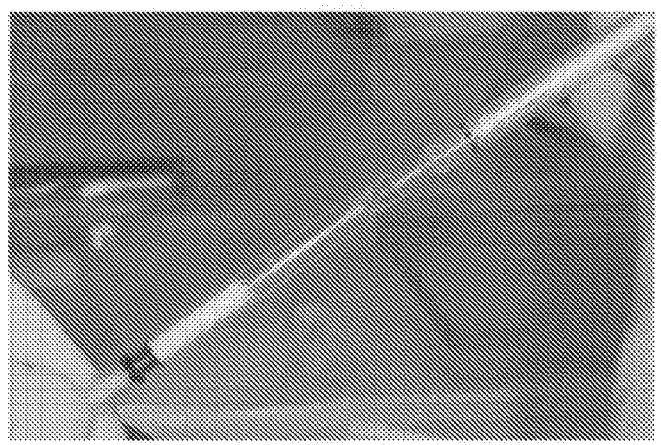

Referring to FIG. 1, the bone graft or biocomposite of the invention is obtained by the steps of a) combining a base material (A) on the basis of granules of beta-tricalciumphosphate and a biodegradable polymer or co-polymer with (b) a first composition (B) which is a dispersion or solution comprising (i) one or more organic compounds having at least one nitrogen-containing basic group which are firstly a plasticizer of the biodegradable polymer or co-polymer and which secondly can form a salt with an acidic protein having a pKI of 4.0, and (ii) substantially pure active human rBSP and (c) optionally, a pharmaceutically acceptable excipient or carrier; to obtain (c) a biocomposite (C) comprising a salt of active human rBSP, plasticizer having at least one basic nitrogen group, bioresorbable polymer or co-polymer and granules of beta-TCP which is moldable and rapidly hardens in situ after placement. As mentioned, the moldable bio-composite (C) can be placed by surgery or prosthetic dentistry and hardens rapidly in situ after placement due to the action of blood and water (D). After hardening, the hardened biocomposite (D) comprises granules of a beta-tricalciumphosphate scaffold and a salt of active human rBSP embedded in a biodegradable polymer or co-polymer.

The key to implant success still is the initial healing process. The bone graft material of the present invention is osteoinductive and osteoconductive and, additionally, furthers the healing of soft tissue, particularly, damaged and diseased connective tissue without becoming resorbed rapidly. In other words, the bone graft material is angiogenic but also provides a physical barrier against an immigration of fibroblasts and cells of the connective tissue as the bioresorption of the hardened beta-tricalcium phosphate scaffold can be adjusted such that it progresses parallely with osseogenesis. The biocomposite of the invention therefore provides macroscopically an early physical support for the dental implant and microscopically a scaffold for cells of the osseous system as well as a nucleus for bone mineralization. Moreover, it furthers angio-genesis as well as wound healing while inhibiting fibrous union.

The moldable biocomposite of the invention has physical and mechanical properties immediately after placement because the granules of tricalcium phosphate in beta-crystal form have been coated with a bioresorbable polymer or co-polymer which harden rapidly when the plasticizer contained in the bioresorbable polymer dilutes out into surrounding body fluids (blood, serum, water, sputum).

As mentioned above, component (A) is first combined according to the invention with a plasticizing agent for the bioresorbable polymer or co-polymer to make the base material moldable for and during placement. The plasticizer or dispersing agent (B) is selected from a group of compounds having a nitrogen-containing basic group so that they can likewise function as carrier and physiological co-ions for acidic glycoproteins such as human rBSP, which has a pKI of 4.0. Plasticizers work by embedding themselves between the chains of the polymer or co-polymer, spacing them apart and increasing of the "free volume", and by lowering the glass transition point of the polymer or co-polymer. Suitable plasticizers and physiological co-ions of the invention are: N,N-diethyl-1,4-butanediamine, 1-(2-aminoethyl)-piperazine, 2-(1-pyrrolidyl)ethyl-amine, 4-amino-2-methoxy-pyrimidine, 2-dimethylaminoethanol, 1-(2-hydroxyethyl)-piperazine, 4-(2-hydroxyethyl)-morpholine, 2-mercaptopyrimidine, 2-mercaptobenz-imidazole. Particularly preferred are N,N-dimethyl-1,3-propanediamine, 4-(2-aminoethyl)-pyridine, 2-amino-6-methoxybenzothiazole, 4-(aminoethyl)pyridine, N,N-diallylmelamine, 3-amino-1,2,4-triazole, 1-(3-aminopropyl)-imidazole, 4-(2-hydroxyethyl)-pyridine, 1-(2-hydroxyethyl)-imidazole, 3-mercapto-1,2,4-triazole. Suitable compounds are characterised by a non-reactive basic group having a pKa-value of from 2 to 14, preferably a pKa-value of from 5 to 14 and most preferably of from 5 to 12. The pKa-value can be obtained from tables. The limiting values given above refer to the measurement of the pKa-value at 25° C. Most preferred is the use of 1-methyl-2-pyrrolidone (NMP=CAS Number: 872-50-4; N-methylpyrrolidone, 1-methylpyrrolidone, N-methyl-α-pyrrolidinone, 1-methylazacyclopentan-2-one, N-methyl-γ-butyrolactone) which is known as enhancing osteoblastic maturation in vitro as well as bone regeneration in vivo (Miguel et al, 2006, Europ. Cells & Materials, 11, Suppl. 2:5). The underlying biological mechanism of this activity however remained in the dark.

The bioresorbable and biocompatible polymer of the invention is preferably an acid copolymer of poly(lactide-coglycolide) PLGA or poly(lactic-co-glycolic acid). PLGA is synthesized by means of a ring-opening co-polymerization of the cyclic dimers (1,4-dioxane-2,5-diones) of glycolic acid and lactic acid. During polymerization, successive monomeric units of glycolic or lactic acid are linked together by ester linkages, yielding a linear, aliphatic polyester as a product. Depending on the ratio of lactide to glycolide used for the polymerization, different forms of PLGA are obtained.

The most preferred is PLGA 75:25 which identifies a copolymer whose composition is 75% lactic acid and 25% glycolic acid. The PGLA glass transition points lie in the range from 40° C. to 60° C. which also depends on the amount of plasticizers or NMP present. Unlike the homopolymers of lactic acid (polylactide) and glycolic acid (polyglycolide) PLGA is dissolved by solvents such as tetrahydrofuran, acetone or ethyl acetate and can therefore be easily coated onto a particulate material such a particles of beta tricalcium phosphate.

PLGA degrades in the presence of water by hydrolysis of its ester linkages to produce the monomers lactic acid and glycolic acid, which can enter various metabolic pathways in the body so that there is no systemic toxicity associated with using PLGA for biomaterial applications. The time required for degradation of PLGA depends partly on the monomers' ratio. PGLA 50:50 is rapidly degraded in vivo within about two months whereas polymers that are end-capped with esters have longer degradation half-lives. The difference in rate of degradation between pure polymers of lactic acid (PLA), glycolic acid (PGA), and various ratios of copolymers of these two substances have been intensely studied in rats and other mammals using implants made of carbon-14 and tritium-labeled polymers. The half-lives of the different polymers and copolymers were calculated from the radioactivity present in the implant area as well as in tissues from the liver, spleen, kidney, lung and of course from the radioactivity present in the urine and feces collected throughout the experiment for each time interval. The half-life of the polymers and copolymers decreased from 5 months for 100% PGA to 1 week with 50:50 PGA:PLA copolymer and rapidly increased to 6.1 months for 100% PLA. No difference in rate of degradation was observed in soft tissue or bone. No significant radioactivity was detected in urine, feces, or other tissue samples. From those studies, it can be concluded that a control of degradation rate of the implant can be best be attained by varying the composition of PLA and PGA between 75% and 100% PLA along with a corresponding 25% to 0% PGA. This would provide a half-life range of the implant of from 2 weeks to 6 months. Such biodegradable polymers are therefore most preferred.

Another bioresorbable polyester is polycaprolactone which can be used for long term implantable devices as its degradation is slower than that of PLGA. Polycaprolacton (tradename Resilon™) has been being investigated as a scaffold for tissue repair and in prosthetic dentistry for root canal filling. Generally, the biodegradable polymer can be selected from a group comprising polyglycolide, polylactides, polycaprolactones, polytrimethylenecarbonates, polyhydroxybutyrates, polyhydroxyvalerates, polydioxanones, polyorthoesters, polycarbonates, polytyrosine-carbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly(amino acids), modified polysaccharides, modified proteins and their copolymers, terpolymers or combinations or mixtures or polymer blends thereof. The polymer matrix is preferably selected from the group consisting of polyglycolide, poly(L-lactide-co-glycolide), poly(D,L-lactide-co-glycolide), poly(L-lactide), poly(D,L-lactide), poly(L-lactide-co-D,L-lactide), polycapro-lactone, poly(L-lactide-co-caprolactone), poly(D,L-lactide-co-caprolactone) polytrimethylenecarbonate, poly(L-lactide-co-trimethylenecarbonate), poly(D,L-lactide-co-trimethylenecarbonate), polydioxanone and their copolymers, terpolymers or combinations or mixtures or polymer blends thereof.

The osteoconductive structural component of the invention preferably is tricalciumphosphate (TCP). If the TCP scaffold degrades too rapidly fibrous union takes place across the openings without osseous repair. If there are too few pores or paths within the scaffold, ossous regeneration is extremely slow. The purity of the TCP influences both bone formation and biocompatibility and TCP in the beta-crystal form (beta-TCP) is most preferred as scaffold. As the scaffold should permit ingress of host osteoblasts and mesenchymal cells an average pore size of about 200 to 400 μm in diameter is preferred as well as pores interconnected via paths of 100 to 200 μm. Porous beta-TCP however has weak mechanical properties and degrades rapidly in vivo. This implies somewhat weak mechanical properties. The beta-TCP of the invention is therefore preferably one sintered at temperatures to obtain a phase pure beta-crystal form for avoiding rapid degradation. In accordance with the invention, the scaffold are therefore preferably fine phase-pure particles of beta-TCP micro-coated with biodegradable polymer and formed for better handling to polymer-coated TCP granules from about 100 to 5000 μm, preferably from 200 to 700 μm for the filling of smaller bone cavities and from 500 to 1500 μm for larger bone cavities, e.g. cavities after resections. Very large polymer-coated beta-TCP granules can be used as osteoconductive scaffold for larger bone replacements in plastic and reconservative surgery.

By mixing the active human rBSP with a plasticizer that embeds into the bioresorbable polymer coated onto granules of a beta-TCP scaffold, the active human rBSP becomes integrated into a bone-mimetic material where it can exert its osteo-inductive activity in an osteoconductive milieu even after hardening. As the employed active human rBSP is preferably underglycosylated and embedded in a polymer or co-polymer it can further escape deactivation by complement factor H and form a nucleus to bone mineralization. The human rBSP is further embedded in a bioresorbable polymer and/or copolymer by means of the plasticizer and therefore released parallely with the bioresorption of the bioresorbable polymer or co-polymer. In summary, the long-term activity of the human rBSP is obtained via (i) the formation of a physiological clathrate or complex salt with the basic nitrogen of the plasticizer; (ii) by its physical incorporation in the bioresorbable polymer or co-polymer which keeps it off from pre-mature mineralization and binding to complement factor H; and (iii) by its underglycosylation as underglycosylated human rBSP is less effectively deactivated by complement factor H than fully glycosylated human BSP from regular bone cells. Thus, the recombinant human rBSP must be obtained from cells cultivated in a serum-free medium. Notwithstanding, the human rBSP remains to be an in vivo nucleus to bone mineralization and calcium phosphate precipitation. The instant invention therefore encompasses a graft composition comprising human rBSP for a repair of damaged bone and connective tissue. As mentioned in the introduction, human bone sialoprotein is beside osteocalcin and osteonectin the major non-collagenous protein in the extracellular matrix of bone.

It is further contemplated having the osteoactive rBSP linked to the scaffold or polymer-backbone via a linker and linker-tags. Human BSP contains however no cysteine residues. Human BSP possesses a high degree of negative charge (pI=4.0) so that a strong anion exchange HPLC was first employed to isolate the BSP complex. The basic group of the plasticizer may therefore exert a similar binding effect.

While the inventors do not wish to be bound by any theory, it is noted that the acidic human rBSP in the composition of the invention has both osteoinductive and biomineralizing effects and promotes adhesion and chemotactic migration of osteoblasts and osteoclasts to the bone graft material. Our findings support that a clathrate or complex salt of human rBSP and the basic plasticizer have synergistic activity, notably with respect to soft tissue and wound healing, when comprised in a biodegradable polymer or co-polymer and optionally with a support or excipient. While each component has biologic activity, the combination provides synergistically useful angiogenic and osteoinductive effects. The provided galenic form is based on a mixture of a biodegradable polymer and granules of a mineral support that can be easily administered at the site of operation where angiogenic and osteogenic activities are need in a defined concerted order. There is strong evidence that human rBSP not only assists in wound-healing and osteogenesis. It does also inhibit inflammation and implantitis in the course of dental surgery. The TCP scaffold in the biocomposite of the invention finally provides a temporary mechanical barrier against fibrous union and endothelial ingrowth so that the biocomposite and the human rBSP can fully develop their osteoinductive effects and promote osseous regeneration. The biodegradable polymer is required in this connection for embedding the human rBSP and its slow release in active form.

In vivo, the expression of BSP coincides with initial bone mineralization and it was shown that BSP is osteoinductive when coated onto femoral implants (OToole G C et al, 2004, J Orth Res 22:641-646.). Similar effects have also been reported for the osteogenic proteins OP-1, BMP-7, various other non-collagenous bone matrix proteins, fibroblast growth factor (FGF), transforming growth factor-β (TGF-β), platelet-derived growth factor (PDGF), insulin growth factor (IGF) and family members of the foregoing. The osseous activity of these bioactive molecules, however, is mere speculation because their osteointegrating activity cannot be measured, neither in vitro nor in vivo.

The biocomposite of the invention however can be directly placed and hardened at the site of the extraction or where osseous regeneration and soft tissue healing is needed. In cases of smaller extractions, the semi-hardened biocomposite can be cut at the level of the surrounding gingiva so that a smooth surface is obtained with only a minimal gap between soft tissue and bone graft material; see FIGS. 4A-C. The bone graft material then heals in within one day or two (see FIG. 4D) while the soft tissue attaches to the bone graft material. Consequently, the flap within the gingiva can be smaller and the entire surgery less heavy for the patient. In cases of smaller dental implants it is even no longer necessary to suture the gingiva over the site of implantation; see FIG. 4C.

Along with the adhesion of osteoclasts and osteoblasts to the bone matrix BSP is further involved in the adhesion, dissemination and orientation of the endothelial cells and in blood vessel formation (Bellahcéne et al., 2000, Circ. Res. 86(8), 885-91). However, fibrous union or endothelial ingrowth is not desired at the site of implant where additional bone is needed for physical support of the enossal implant. This is achieved according to the invention by having granules of beta-TCP in the biocomposite.

Notwithstanding, the human rBSP suppresses inflammation reactions and modulates the release of proteins involved, namely of interleukins IL-6, IL-8, RANKL, osteoprotegerin (OPG), etc.

The invention provides a novel bone graft and composite material which promotes differentiation of mesenchymal stem cells to osteoblasts, induces osteoblast migration to the site of required osseous regeneration as well as osteoblast proliferation and finally provides a nucleus for bone mineralisation. Numerous proteins have been investigated for their osteogenic properties and notably collagen, fibronectin, vitronectin as well as mixtures of natural extracellular matrix proteins (Sodek et al, J, 2000, Peridontol., 24:99-126; Meyer U et al, 1998, J Mater Sci-Mater Med 9:301-307; Lacouture M E et al., 2002, J Bone Miner. Res 17:481-492; Salih E et al, 2002, Biochem J. 364:465-474). By comparison of type I collagen, fibronectin, and vitronectin in supporting adhesion of mechanically strained osteoblasts it was revealed that the major factor governing strain resistance was the number of the integrin-extracellular matrix attachments when the number of molecules available for attachment was limited (Lacouture M E et al., 2002 J Bone Miner Res 17:481-49220). Thus, it is contemplated having also those proteins incorporated in the biocomposite of the invention.

In the prior art, there are no means available to obtain physiological improvements in the initial healing process (Lekic P et., 1996, Anat Rec 244:50-58). This is because any large surface area of biomimetic graft materials leads to delayed cell proliferation. There were further no methods or compositions available for an administration of BSP such that it can exert its biological functions in vivo and is not deactivated either by complement factor H or mineralization, while the deposition of BSP represents in vivo the first step to bone formation (Riminucci M et al., 2003, Braz J Med Biol Res 36:1027-1036). Moreover, BSP was found to be osteoinductive in bone repair and to achieve healing in critical defects (Wang M L of al., 2002, J Orth Res 20:1175-1184; Wang J et al, 2004 J Bone Miner. Res. 19: 221 Abstract). Thus, efforts have been made as to induce the expression of BSP by inductive agents (Chou et al., 2005, Biomaterials 26:285-29529). These efforts however turned out as not successful.

It can be speculated that BSP undergoes some kind of extracellular maturation which reduce its differentiating and proliferating potential on mesenchymal stem cells and osteoblasts. Some research groups have even hypothesized that BSP protects trophoblasts and BSP-producing tumors cells from attack by the immune system as it binds with high affinity the factor H of the complement system, which is known to restrict the alternative path of the complement lysis (Fedarko et al., J. Biol. Chem., 200, 275, 16666-16672; WO 00/062065). However, it is proven that BSP specifically binds in vivo to the integrin receptors through its recognition sequence arginine-glycine-aspartate, RGD. The binding of the RGD recognition sequence to the alpha(v) beta(3) integrin receptors and because of the observation that adhesion, dissemination and orientation of the endothelial cells is mediated by BSP, BSP stands at the centre of events in the formation of bone matrix and wound healing. Moreover, blood vessel formation around a tumor occurs in parallel with the BSP expression in the tumor cells (Bellahcéne et al., 2000, Circ. Res. 86(8):885ff). However, "free" BSP is bound by complement factor H with high affinity so that any administered BSP by prior art compositions could not exert its physiological functions. The large factor H molecule of 150 kDa binds the smaller BSP (of ca. 65 kDa) to such an extent that antibodies or receptors cannot bind. Further, factor H is present in excess in the serum (0.5 mg factor H/mL in comparison to BSP with <20 ng/ml serum in the case of healthy persons).

Our data however indicate that low concentrations of underglycosylated human rBSP are sufficient to induce differentiation of mesenchymal stems cells and initial attachment of osteoblasts. This is achieved by having the underglycosylated human rBSP integrated in a biodegradable polymer so that differentiation and settlement of bone cells are no longer retarded by a large surface or foreign material. The underglycosylated human rBSP of the invention however is still highly acidic and reacts and precipitates with hydroxy groups and calcium phosphate. By dissolving underglycosylated human rBSP coating in a basic solvent and plasticizer for the bioresorbable polymer, it seems that the BSP protein is kept in a state wherein it can exert longer its biological functions. The underglycosylated human rBSP is most preferably incorporated in a scaffold made of granules of beta-TCP which pores preferably have a diameter size of 10 to 1000 μm, more preferably, 20 to 500 μm, most preferred 50 to 200 μm. In other words, a mineralized or bony osteointegration of the bone graft can be achieved when the osteoblasts attach and grow indeed into the pores of the graft material. Thus, the pores should preferably have a diameter size of 10 to 1000 μm, more preferably, 20 to 500 μm, most preferred 50 to 200 μm. The underglycosylated human rBSP is comprised in the composition of the invention preferably in a concentration of 1 to 100 μg/mL, preferably 10 to 50 μg/mL.

The examples and embodiments of the invention described herein below shall not be construed as limiting or otherwise restricting but rather examplary in nature only. The scope of the invention has been defined in the attached claims.

EXAMPLES

All of the procedures used in the present experiments were approved by the Ethics Committee. The rules of the Declaration of Helsinki 1964 (NIH publication no. 86-23, revised 1985) were followed.

Example 1

Preparation of an Angiogenic Mixture with Osteoinductive Human rBSP

The underglycosylated human rBSP was isolated according to the method described by Wuttke et al. (Wuttke et al, 2001, *Structural characterization of human recombinant and bone-derived bone sialoprotein*. J Biol Chem 276:36839-36848). In brief, the complete cDNA for human BSP (without signal peptide) was amplified by means of PCR and cloned in the episomal eucaryotic expression vector pCEP-Pu (Kohfeldt E et al., *Properties of the extracellular calcium binding module of the proteoglycan testican*, in FEBS Lets. 1997, 414(3) 557-61). The expression constructs were introduced by means of liposome mediated stable transfection into the embryonic kidney cell line EBNA-293 or human breast cancer cells MCF-7. Transient cells were cultivated, 48 hours after transfection for two days in serum-free medium so that the proteins in the FCS could not react with the expressed rBSP and interfere with the purification of the recombinant BSP. BSP expressing cells were then cultivated under serum free conditions. The expression of the recombinant human BSP was monitored through SDS-PAGE and immunoblots.

2.5 liter serum-free culture supernatant of transfected cells was purified via a Sepharose™ column and the yield therefrom was 250 μg homogeneous recombinant His-myc-EK-BSP (human rBSP). The human rBSP was partially glycosylated and had no glycosylation at threonine 125. The amino acid sequence of human rBSP contains four N-glycosylation sites at the positions 88 (NTT), 161 (NCT), 166 (NST) and 174 (NGS). All identified N-glycane structures could be found both on the recombinant EBNA-293 BSP. There were however differences in the percentage proportion of the respective structures in the total N-glycanes. The main proportion of the BSP N-glycanes from bone was of triantenary structures (58%) and in the EBNA cell line of tetraantenary structures (48%). By means of MALDA-TOF mass spectrometry the masses of the peptides were determined and a part of the peptides sequenced by means of PSD-MALDI-TOF mass spectrometry. Of these, the threonines in the human rBSP sequence DATPGTG are O-glycosylated. With BSP isolated from human bones there was effected a third O-glycosylation. With recombinant BSP no third glycosylation site is present. Probably, this glycosylation site lies on the TGLAA-BSP part structure.

250 μg of human rBSP isolated from cells cultivated under serum-free conditions was then freeze-dried and dissolved in 5 mL N-methylpyrrolidone to obtain a basic solution comprising human rBSP (50 μg/mL) having angiogenic and osteoinductive activity.

Example 2

Preparation of a Moldable Bone Graft and Biocomposite with Osteo-Conductive Properties As bone graft and osteoconductive material, there was used a commerical Easy Graft™ "spaceholder" material of DS DENTAL Degradable Solutions AG (Schlieren-Zürich, Wagistrasse, Switzerland). The biocomposite comprised granules of pure tricalciumphosphate (TCP) in the beta-crystal phase. The TCP-material had been compacted to granules and in the present example there was used the fraction wherein the granula had diameters from 500 μm to 630 μm, a microporosity of greater than 50 percent and an average pore size of about 5 μm. For facilitating placement the granules of the commercial Easy Graft™ spaceholder material are further coated with a 10 μm layer of biodegradable PLGA polymer so that the hard granula material can be made moldable for placement by the addition of a defined amount of plasticizer.

Example 3

Preparation of a Biocomposite and Spaceholder Having Osteoinductive, Osteoconductive and Angiogenic Properties The biocomposite of the invention was prepared by immersing and impregnating PLGA-coated granules of beta-TCP (Easy Graft™ "spaceholder" material of DS DENTAL Degradable Solutions AG, Schlieren-Zürich, Wagistrasse, Switzerland) with a basic organic plasticizer solution comprising N-methyl-2-pyrrolidone (NMP) and 50 μg/mL human rBSP for a period of 5 seconds to 1 minute with gentle agitation so that the hardened granular TCP-material becomes flowable and liquid clathrates are obtained of a multidentate human rBSP-NMP complex salt which is embedded within the biodegradable PLGA-coating. As the biodegradable PLGA is located at the surface of the compacted TCP material, within the TCP channels and pores and further within inter-granular gaps and crevices, the clathrates of human rBSP NMP complex salt was thereby also enshrined within the granular beta-TCP material. Consequently, a biocomposite was obtained comprised of granules of pure tricalciumphosphate (TCP) in the beta-crystal phase, a biodegradable PLGA polymer and enshrined clathrates of NMP and biologically active human rBSP. The biocomposite material was moldable during placement and hardened in situ after placement by diffusion of excessive NMP into water and blood within 2 minutes. The component of the biocomposite were preferably mixed in such a ratio that the resulting hardened biocomposite was expected to comprise about 20 µg human rBSP per milliliter of beta-TCP/PLGA material (EasyGraft™ space holder) after hardening.

Figure 2C:
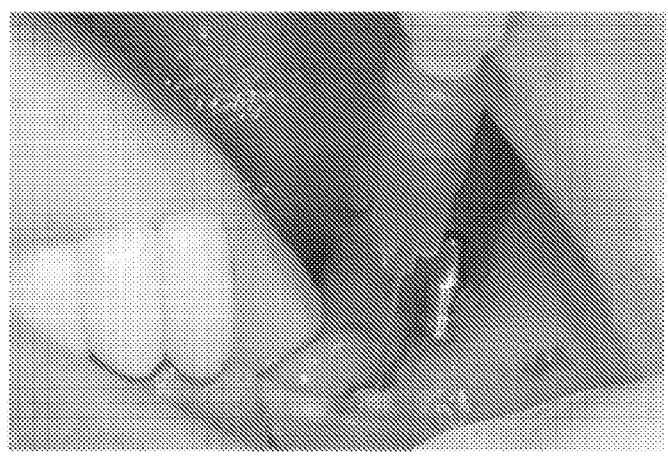
Figure 3A:
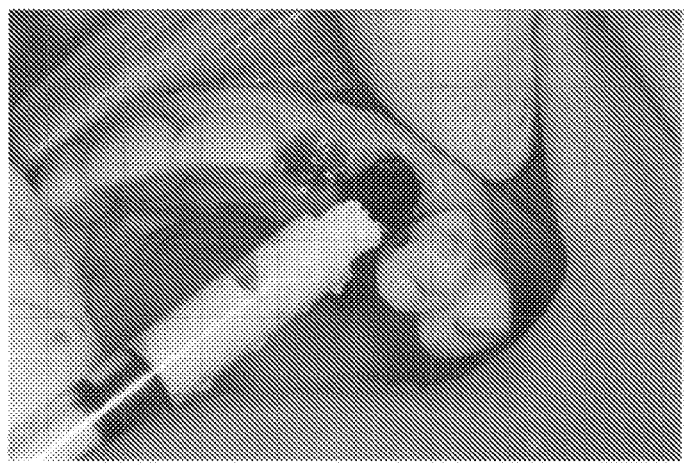
FIGS. 3A-C are photos of a surgical placement and hardening in situ of the biocomposite of the invention.
Figure 3B:
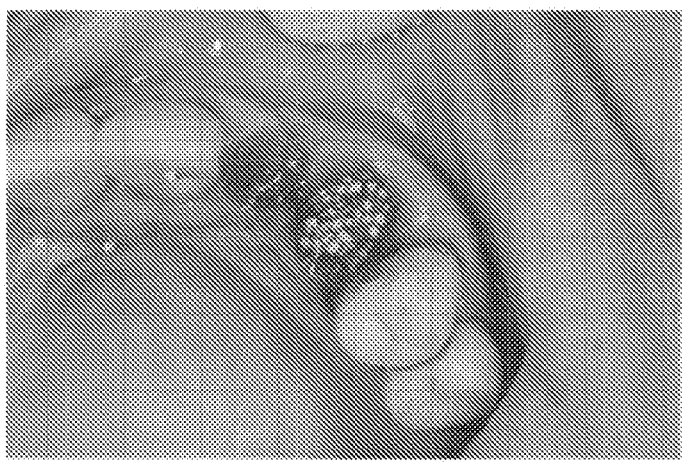
Figure 3C:
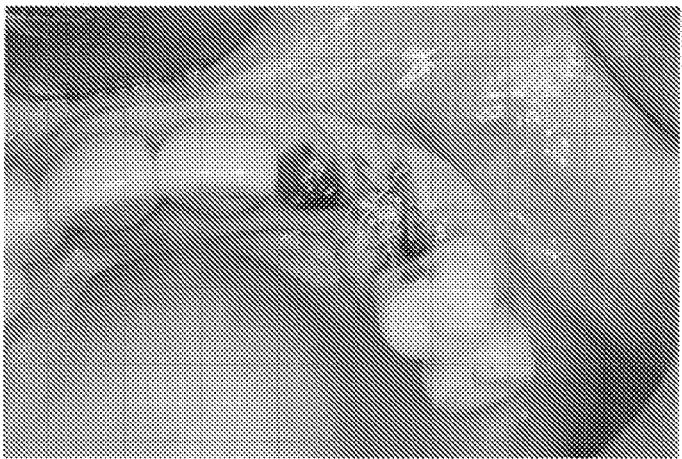

The mixing with the granular TCP material was either done extra-corporal by a syringe device or ampule (see FIGS. 2A, B) or alternatively in situ when a portion of the TCP-material has been placed for in situ molding (FIG. 2C).

Example 4

Surgery

FIGS. 4A-H and 4J-K describe the application of the biocomposite in surgical dentistry and for bone formation. Clinically, the healing times and in particular soft tissue healing turned out to be 50% faster and complete which goes in line with an active inhibition of implantitis and activation of tissue and wound healing. Reaction times in wound healing are practically halved (50%) and generation of bone material doubled, compared to regular Easy Graft™ material with NMP as plasticizer for molding. Bone density measurement are being done to quantify the BSP/NMP-accelerated soft and hard tissue healing. The biopsy of implants (biocomposites) taken shortly after implantation suggest that BSP-induced newly formed bone material is histologically indistinguishable from natural bone tissues which confirms the observed rapid ingress of osteoblasts and natural bone mineralisation processes in line with the observed accelerated regeneration and natural lesion healing.

Figure 4A:
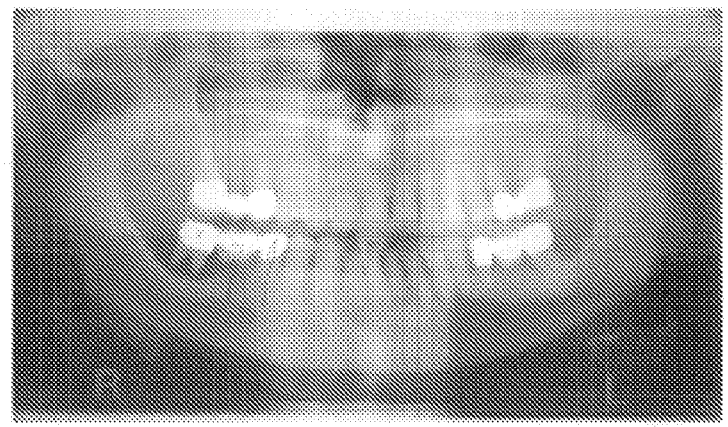
FIGS. 4A-D are photos of the placement site (patient ♀, 73 years) and the wound healing 1 day post operation, 3 weeks post operation.
Figure 4B:
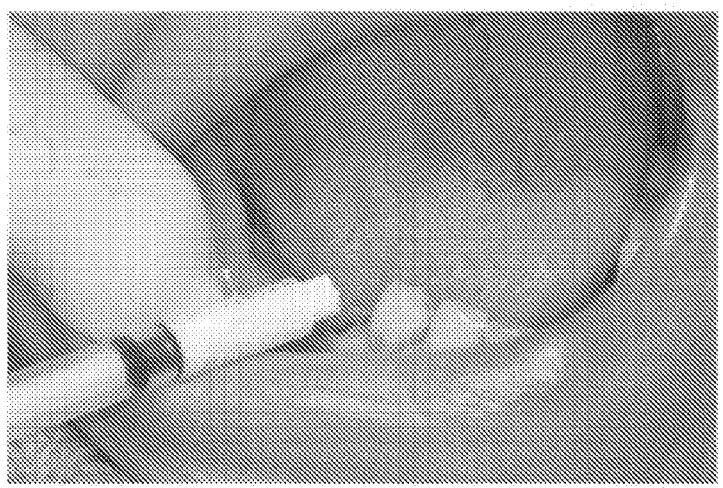
Figure 4C:
Figure 4D:
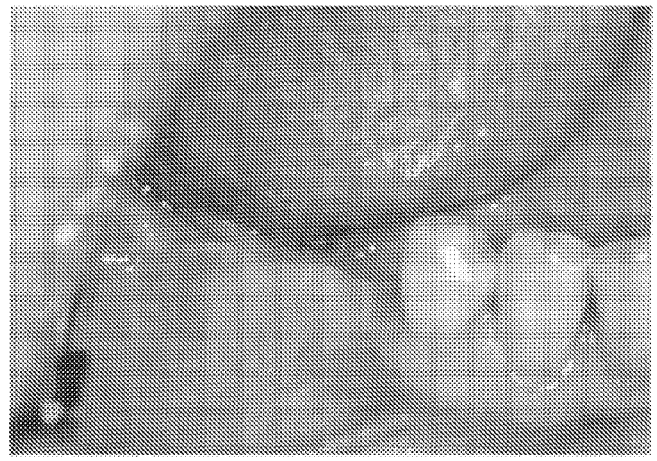
Figure 4E:
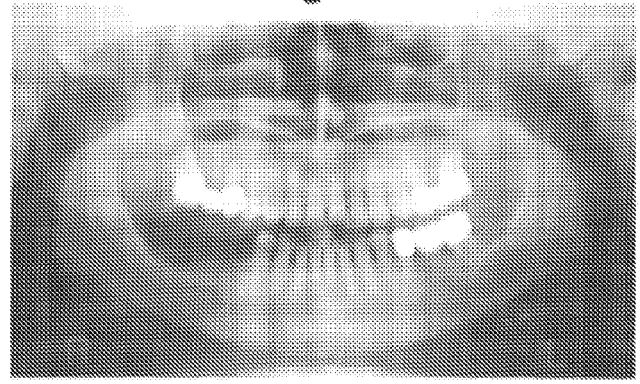
FIG. 4E-G are X-rays and CTs 2.5 months post operation and showing the situation prior to implantation and dentistry.
Figure 4F:
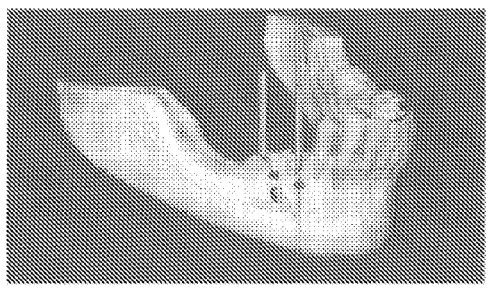
Figure 4G:
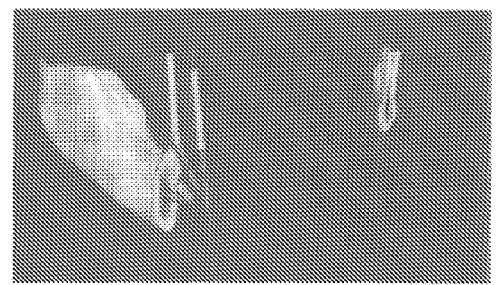
Figure 4H:
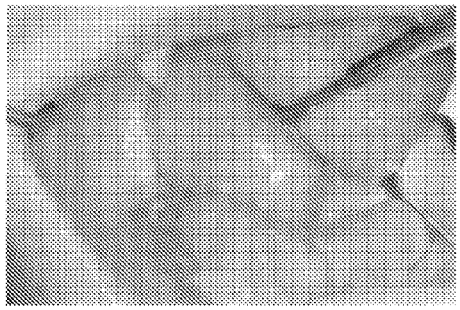
FIGS. 4H and 4J-N are photos of an exemplary dentistry following wound healing and bone regeneration.
Figure 4J:
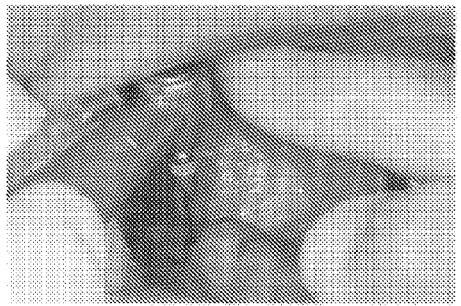
Figure 4K:
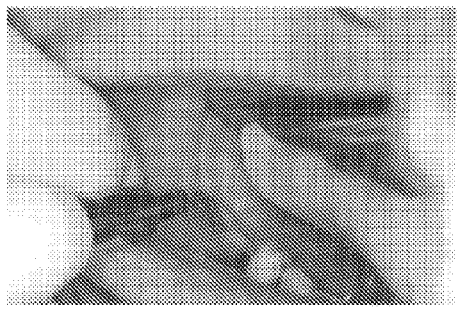
Figure 4L:
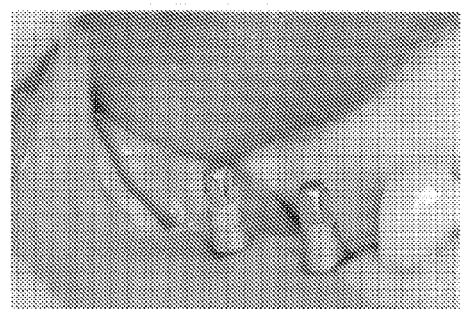
Figure 4M:
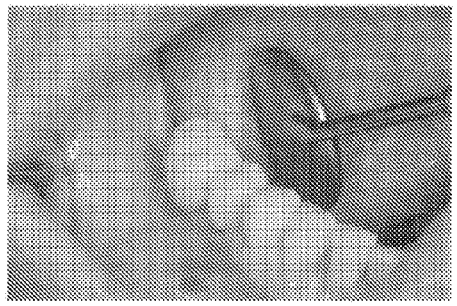
Figure 4N:
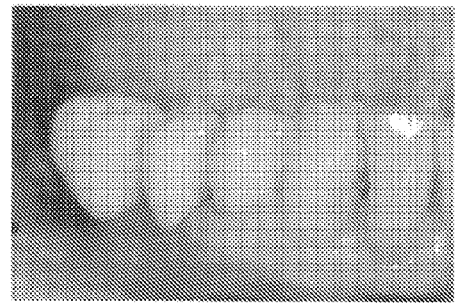

FIG. 4A is an X-ray showing the dental and bone situation of a patient (female, 73 yrs) prior to surgical dentistry. FIG. 4B shows the placement of a moldable bone graft (EasyGraft™) impregnated and comprising a preformed mixture of human rBSP/NMB (50 µg human rBSP/NMP per mL granular TCP/PLGA). Excessive granular graft was removed (cut off) before final hardening and the gingiva flap manually pressed and closed without suture. FIGS. 4C and 4D show the clinical situation 1 day and 3 weeks post operation. Note the accelerated initial wound healing and the short complete soft tissue healing for elderly patients. FIGS. 4E and F are an X-ray and CT 2.5 months post implantation showing the newly formed bone in the crestal region of 1113 HU. Note the interproximal level of newly formed bone. FIG. 4G shows how the dental implants (screws) would be placed. FIGS. 4H and 4J-N show exemplary the steps of the following dentistry, namely the placement of positioning device (4H), the placement of bleeding points (4I), the lateral piezo compaction of the bone at the implant site (4K), the implants after positioning (4L). Note the width (3 mm) and interproximal distance for preservation of the papillae (>3 mm). The provisionary (4M) and the final dental solution (4N).

Notably, FIGS. 4C to 4F confirm the accelerated tissue and wound healing when the granular TCP graft material has been treated with human rBSP. FIG. 4E moreover confirms that rapid soft tissue healing does not hamper or interfere with osteoinductive and osteogenic properties of the bone graft material and that the human rBSP can fully excert and develop its osteoinductive activities when embedded in a biodegradable polymer.

Example 5

Histologic Examination of Placed Biocomposites after

Biocomposites of the invention were placed after tooth extraction and bone specimens taken 12 weeks after surgery (lengths—D68: 1.2 cm; D78: 0.5 cm; D59: 0.6 cm). The trepan cores were dehydrated, embedded in a polymerizable resin material and hardened blocks containing the tissue samples cut to 2-to-3-micrometer-thick tissue sections. The tissue sections which are mounted on a glass microscope slide for general staining with Masson's trichrome stain (Masson-Goldener), toluidine blue and haematoxilin paired with eosine.

In the Masson's trichrome stain: nuclei are black; cytoplasm—red/pink; RBC—red; collagen fibers and cartilage—blue/green; muscle fibers—red.

In the general H & E staining (heamatoxylin paired with eosin), nuclei, nucleic acids and ER are blue; cytoplasm—pink; RBC—orange/red; elastic fibers, reticular fibers and collagen fibers—pink.

In the general staining with toluidine blue, nuclei and nucleic acids, cytoplasm, RBC and collagen fibers are blue and mast cells granules purple due to the lower pH.

Figure 5:
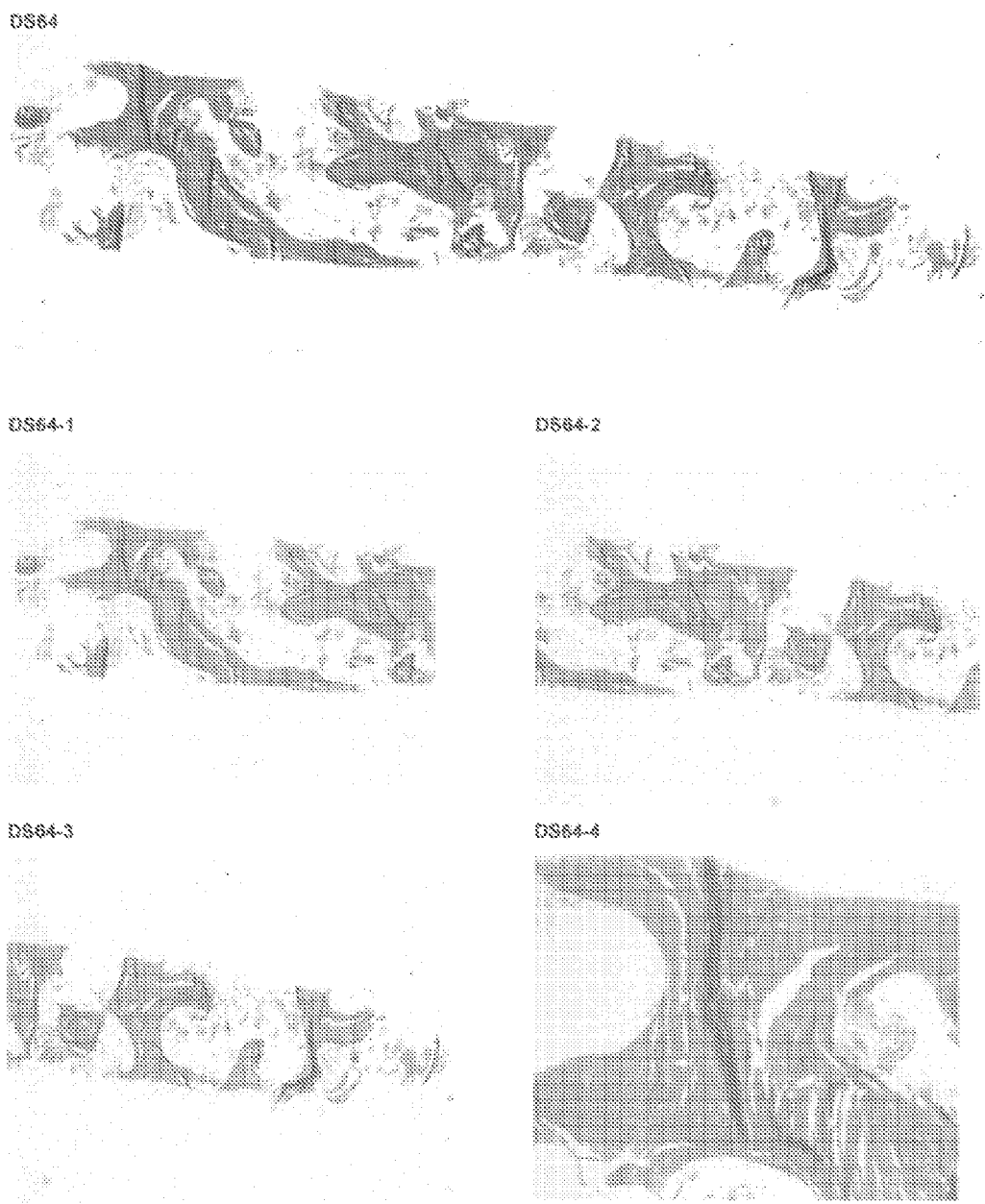
FIG. 5/01-13 microscopic views of a bone specimen (DS64—length 1.2 cm) taken from a placed rhBSP/TCP-biocomposite in accordance with the invention 12 week weeks after surgery—staining of histologic sections of 2 to 3 micrometer thickness with Masson-Goldner's trichrome stain or toluidine blue or haematoxylin paired with eosin.

Referring to FIG. 5, the overview of section DS64 (Dünnschnitt #64) of the specimen (Masson-Goldner staining) displays under 10-fold magnification vital ingrowth of bone tissue while some foreign granular material (beta-TCP granules) is visible. On views DS64/01-03 osseoneogenesis prevails and the proportion of foreign material is less. At higher magnification view DS64/04 shows early stages of lamellar bone formation (after 12 weeks only!) and an early onset of lamellar bone formation. Usually, lamellar bone can only be detected in such kind of specimens after nine months or so. Views DS64/05-07 display isolated zones of foreign material but there are clear signs of vital osseoneogenesis at some locations. Microscopic views DS64/08-10 are based on H&E staining at different magnifications. The microscopic views show early stages of newly formed lamellar bone and, at higher magnifications, chains of osteoblasts in the peripheral portion. Views D64/11-13 have been stained with toluidin. Successful regeneration and newly formed bone material can be found within the trepan core.

Referring to FIG. 6, the overview of specimen DS78 shows less osseoneogenesis within the trepan core. At higher magnifications, there are indicia for woven bone; see microscopic views DS78/11-13. Thus, maturation of woven bone to lamellar bone is going to take place.

Referring to FIG. 7 and with respect to specimen DS59, the overview (DS59-9) of the left end of the trepan core shows far reaching bone reconstruction and vital osseoneogenesis with only some traces of foreign material. The overview (DS59-06) of the right end of the trepan core shows likewise vital osseoneogenesis and bone reconstruction. The newly formed bone material is of lamellar type as can be seen on microscopic view DS59/07. This stands of very active neogenesis. View DS59/09 shows islets of vasculogenesis and anginogenesis, say fibroblasts, osteoblasts as well connective tissue formation and all signs of bone reconstruction and osseoneogenesis.

In summary, specimens 64 and 59 show an early onset and pre-potent oseeoneogenesis. Specimen 78 shows less bone formation. In all cases, histology revealed robust new woven and lamellar bone formation with only minimal traces of residual foreign material. Thus, the new biocomposite of the invention appeared to have undergone accelerated remodeling and induced bone reconstruction and bone formation.

Example 6

In Vitro Activity of Human rBSP on Osteoclasts

The activation and differentiation of osteoclasts is reliant on the expression of RANKL from osteoblasts as well as on the expression of OPG (osteoprotegerin). OPG seems to counter the activity of RANKL and to inhibit differentiation of osteoclasts. When primary human osteoblasts were incubated in vitro with human rBSP and the expression of OPG and RANKL determined in the supernatant via ELISA and real-time PCR then it was found that the human rBSP generally suppressed the expression of RANKL from osteoblasts and stimulated the release of OPG. An increased rate of RANKL/OPG stands for the activation of osteoclasts which may explain the osteoinductive properties of the biocomposite of the invention.

The invnetion claimed is:

1. A method of making a bone graft material having osteoinductive and osteoconductive properties for treating osseous defects and neogenesis of bone, which bone graft material is a composite of a biodegradable polymer and granules of beta-tricalciumphosphate, the method comprising the steps of:
providing an osteoinductive mixture, which is a dispersion or solution of:
an organic compound having at least one nitrogen-containing basic group, wherein the organic compound is a plasticizer that can form a salt with an acidic protein having a pKI of 4.0, and
a physiologically effective amount of underglycosylated recombinant human BSP obtained under non-denaturing conditions, where the underglycosylated recombinant human BSP is present in said osteoinductive mixture as a salt or complex which has reduced affinity for calcium, hydroxyapatite and complement factor H than regular human BSP present in human serum, and, optionally, a pharmaceutically acceptable excipient or carrier;
providing an osteoconductive mixture on the basis of granules of tricalcium diphosphate ($Ca_3(PO_4)_2$) in beta crystal form, which granules are coated with a biodegradable polymer or co-polymer and, optionally, a pharmaceutically acceptable excipient or carrier, which osteoconductive mixture is moldable and shapable and rapidly hardening in situ when placed by surgery or prosthetic dentistry, and
combining said osteoinductive and osteoconductive mixture shortly before or during placement to obtain a bone graft material which furthers osseous repair and the healing of damage or diseased tissues and lesions.

2. The method of making a bone graft material of claim 1, wherein the osteoinductive human BSP is underglycosylated human BSP expressed and obtained from eukaryotic cells grown under serum-free conditions.

3. The method of making a bone graft material of claim 1, wherein the human BSP has been obtained from colostrum or mother milk.

4. The method of making a bone graft material of claim 1, wherein said organic compound is selected from an organic compound having at least one ring nitrogen-containing basic group and an organic compound having at least one ring nitrogen-containing basic group and being both a dispersing agent and a plasticizer of the biodegradable polymer or co-polymer.

5. The method of making a bone graft material of claim 1, wherein the organic compound is selected from the group consisting of N-isopropylpyrrolidone, N-methyl-pyrimidine, N-ethylpyrimidine, N-methylpyrrolidone (1-methyl-2-pyrrolidone), N-ethylpyrrolidone, N-propylpyrrolidone, N,N-diethyl-1,4-butanediamine, 1-(2-aminoethyl)-piperazine, 2-(1-pyrrolidy)ethylamine, 4-amino-2-methoxy-pyrimidine, 2-dimethylaminoethanol, 1-(2-hydroxyethyl)-piperazine, 4-(2-hydroxyethyl)-morpholine, 2-mercaptopyrimidine, 2-mercaptobenzimidazole, N,N-dimethyl-1,3-propanediamine, 4-(2-aminoethyl)-pyridine, 2-amino-6-methoxybenzothiazole, 4-(aminoethyl)pyridine, N,N-diallylmelamine, 3-amino-1,2,4-triazole, 1-(3-aminopropyl)-imidazole, 4-(2-hydroxyethyl)-pyridine, 1-(2-hydroxyethyl)-imidazole, 3-mercapto-1,2,4-triazole.

6. The method of making a bone graft material of claim 1, wherein said biodegradable polymers or copolymers are selected from the group consisting of polyglycolide, poly(L-lactide-co-glycolide), poly(D,L-lactide-co-glycolide), poly (L-lactide), poly(D,L-lactide), poly(L-lactide-co-D,L-lactide), polycaprolactone, poly(L-lactide-co-capro-lactone), poly(D,L-lactide-co-caprolactone) polytrimethylenecarbonates, poly(L-lactide-co-trimethylenecarbonate), poly(D, L-lactide-co-trimethylenecarbonate), polydioxanones, polylactic acid polymers, polyglycolic acid polymers, copolymers of polylactic acid and polyglycolic acid, polyhydroxybutyrates, polyhydroxyvalerates, polydioxanones, polyorthoesters, polycarbonates, poly-tyrosinecarbonates, polyorthocarbonates, polyalkylene oxalates, polyalkylene succinates, poly(malic acid), poly(maleic anhydride), polypeptides, polydepsipeptides, polyvinylalcohol, polyesteramides, polyamides, polyanhydrides, polyurethanes, polyphosphazenes, polycyanoacrylates, polyfumarates, poly (amino acids), modified polysaccharides, modified proteins and their copolymers, terpolymers or combinations or mixtures or polymer blends thereof.

7. The method of making a bone graft material of claim 1, wherein said osteoconductive mixture comprises coated granules of tricalcium phosphate ($Ca_3(PO_4)_2$) having diameters of 300 to 800 μm for use in prosthetic dentistry.

8. The method of making a bone graft material of claim 1, wherein said composite comprises more than 50 volume percent of granules of beta tricalcium phosphate, between 10 to 40 volume percent of a polymer base including one or more biodegradable polymers and copolymers, 0.5 to 10 volume percent of a first osteoinductive mixture which increases plasticity and workability of the biocomposite and as solvent or dispersing agent of BSP.

9. The method of making a bone graft material of claim 1, wherein said composite comprises human BSP in an amount from 10 to 200 ng/mL (w/v) composite.

10. The method of making a bone graft material of claim 1, wherein said osteoinductive mixture comprises human BSP in an amount from 10 to 200 μg/mL (w/v) before hardening.

11. The method of making a bone graft material of claim 1, wherein said biodegradable polymer is a copolymer of polylactic acid and polyglycolic acid whose composition is 50 to 80 per cent lactic acid and 20 to 50 per cent glycolic acid and a PLA:PGA co-polymer having a weight average molecular weight range between about 25,000 and about 1,000,000.

12. The method of making a bone graft material of claim 1, wherein the bone graft material has a Young's Modulus between 1 GPa and about 100 Gpa after hardening.

13. A method of making a bone graft material having osteoinductive and osteoconductive properties comprising the steps of:
  providing an osteoinductive mixture, which is a dispersion or solution on the basis of: an organic compound having at least one nitrogen-containing basic group, wherein the organic compound is a plasticizer that can form a salt with an acidic protein having a pKI of 4.0, and a physiologically effective amount of underglycosylated recombinant human BSP obtained under non-denaturing conditions;
  providing an osteoconductive mixture on the basis of granules of tricalcium diphosphate ($Ca_3(PO_4)_2$) in beta crystal form, which granules are coated with a biodegradable polymer or co-polymer; and
  combining said osteoinductive and osteoconductive mixtures to obtain a composite material which is initially moldable and shapable and hardens in situ when placed by surgery or prosthetic dentistry.

14. A method of providing a bone graft material with properties which further the healing of wound and soft tissue lesions, comprising the step of combining the bone graft material with a dispersion or solution on the basis of an organic compound having at least one nitrogen-containing basic group, wherein the organic compound is a plasticizer that can form a salt with an acidic protein having a pKI of 4.0, and a physiologically effective amount of underglycosylated recombinant human BSP obtained under non-denaturing conditions.

15. A method of making a bone graft material as recited in claim 1, and then furthering the healing of wound and soft tissue lesions by the application of the bone graft material to the wound or soft tissue lesions.

16. The method of making a bone graft material as in claim 1, wherein said osteoconductive mixture comprises coated granules of tricalcium phosphate ($Ca_3(PO_4)_2$) having diameters of 400 to 700 μm.

17. The method of making a bone graft material as in claim 1, wherein the organic compound can form a salt with an acidic protein having a pKI of 4.0.

* * * * *